United States Patent [19]
Brown et al.

[11] Patent Number: 5,783,729
[45] Date of Patent: Jul. 21, 1998

[54] CHEMICAL PROCESS FOR THE PRODUCTION OF SULFONYL BENZOIC ACIDS

[75] Inventors: Stephen Martin Brown, Huddersfield; Martin Charles Bowden, Brighouse; Keith Moorhouse, Huddersfield, all of United Kingdom

[73] Assignee: Zeneca Limited, London, England

[21] Appl. No.: 751,272

[22] Filed: Nov. 18, 1996

Related U.S. Application Data

[63] Continuation of Ser. No. 240,352, May 10, 1994, abandoned.

[30] Foreign Application Priority Data

May 24, 1993 [GB] United Kingdom ............ 9310699

[51] Int. Cl.$^6$ .................................................. C07C 51/16
[52] U.S. Cl. ........................................ 562/409; 562/422
[58] Field of Search ............................... 562/409, 422

[56] References Cited

U.S. PATENT DOCUMENTS

| | | | |
|---|---|---|---|
| 3,504,022 | 3/1970 | Bresson | 260/524 |
| 3,692,828 | 9/1972 | Onopchenko | 260/524 |
| 3,812,159 | 5/1974 | Lubowitz | 562/409 |
| 3,878,240 | 4/1975 | Kuenzy | 562/409 |
| 4,503,245 | 3/1985 | Giacobbe | 562/414 |
| 4,695,673 | 9/1987 | Heather et al. | |
| 4,780,127 | 10/1988 | Michaely et al. | |
| 4,914,231 | 4/1990 | Manami | 562/429 |
| 4,954,165 | 9/1990 | Baba | 562/409 |
| 4,965,406 | 10/1990 | Dakka | 562/414 |
| 4,990,659 | 2/1991 | Jihad | 562/416 |
| 5,087,724 | 2/1992 | Tanaka | 558/425 |
| 5,155,258 | 10/1992 | Kamiya | 562/429 |
| 5,175,351 | 12/1992 | Rohrscheid | |

FOREIGN PATENT DOCUMENTS

| | | |
|---|---|---|
| 9006302 | 6/1990 | WIPO |
| 9013537 | 11/1990 | WIPO |

OTHER PUBLICATIONS

Journal of Medicinal Chemistry, vol. 17, No. 9, Sep. 1974, pp. 933–930, B.F. Cain et al: Potential Antitumor Agents. 14. Acridylmethanesulfonanilides.

Journal of Organic Chemistry, vol. 51, No. 15, Jul. 25, 1986, pp. 2880–2883, Y. Sasson et al.: Liquid–Phase Oxidation of Deactivated Methylbenzenes by Aqueous Sodium Hypochloride Catalyzed by Ruthenium Salts under Phase-Transfer Catalytic Conditions.

*Primary Examiner*—Michael L. Shippen
*Attorney, Agent, or Firm*—Marian T. Thomson

[57] ABSTRACT

A process for preparing a compound of formula (I),

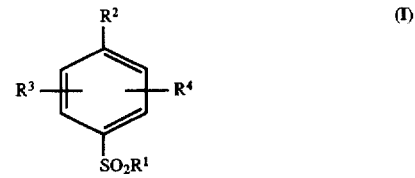

where $R^1$ is optionally substituted alkyl or phenyl, $R^2$ is COOH, and $R^3$ and $R^4$ are independently selected from hydrogen, halo, haloalkyl, nitro, hydroxy, alkoxy, haloalkoxy or alkoxyalkoxy; which process comprises oxidising a compound of formula (II)

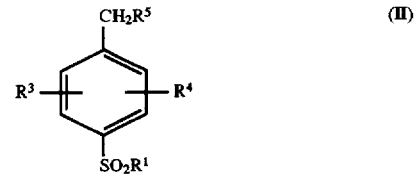

where $R^1$, $R^3$ and $R^4$ are as defined in relation to formula (I) and $R^5$ is H, halo or $C_{1-4}$ alkyl with sodium hypochlorite or sodium chlorite in the presence of a catalytic amount of a ruthenium or palladium compound and a phase transfer catalyst in an organic solvent at a pH of 7–11.

29 Claims, No Drawings

CHEMICAL PROCESS FOR THE PRODUCTION OF SULFONYL BENZOIC ACIDS

This application is a continuation of application Ser. No. 08/240,352, filed May 10, 1994, now abandoned.

The present invention relates to the production of sulphonyl benzoic acids by oxidation of sulphonyl alkyl benzene derivatives.

Sulphonyl benzoic acids are useful as intermediates in the preparation of agrochemicals in particular herbicides as described for example in U.S. Pat. No. 4,695,673 and U.S. Pat. No. 4,780,127.

Known methods of producing sulphonyl benzoic acids by oxidation of sulphonyl alkyl benzene derivatives require harsh reaction conditions. In WO 90/6302 a process is described which requires the use of strongly acid conditions (70% nitric acid) and temperatures of over 170° C. The processes described In WO 90/13537 and EP 505965-A required elevated pressure and a temperature of greater than 120° C. There is therefore a continuing need for a process which can be performed under milder conditions.

According to the present invention there is provided a process for preparing a compound of formula (I), where $R^1$ is optionally substituted alkyl or phenyl, $R^2$ is COOH, and $R^3$ and $R^4$ are independently selected from hydrogen, halo, haloalkyl, nitro, hydroxy, alkoxy, haloalkoxy or alkoxyalkoxy; which process comprises oxidising a compound of formula (II), where $R^1$, $R^3$ and $R^4$ are as defined in relation to formula (I) and $R^5$ is H, halo or $C_{1-4}$ alkyl with sodium hypochlorite or sodium chlorite in the presence of a catalytic amount of a ruthenium or palladium compound and a phase transfer catalyst in an organic solvent at a pH of 7-11.

As used herein the term "alkyl", refers to straight or branched chains having for example up to 20 carbon atoms. The term "haloalkyl" refers to an alkyl group substituted by at least one halogen such as fluorine and chlorine. Similarly the term "haloalkoxy" refers to an alkoxy group substituted by at least one halogen such as fluorine and chlorine. As used herein the term "halo" refers to fluoro, chloro, bromo and iodo.

Suitable optional substituents for the alkyl and phenyl groups $R^1$ include halogen such as fluorine and chlorine.

Preferably $R^1$ is a $C_{1-6}$ alkyl group such as methyl or ethyl; trifluoromethyl or phenyl. Most preferably $R^1$ is methyl.

Suitably $R^3$ and $R^4$ are selected from hydrogen, chloro, nitro, hydroxy, trifluoromethyl or $C_{1-2}$ alkoxy. Preferably $R^3$ is H. The group $R^4$ is preferably ortho to the group $R^2$. A preferred group $R^4$ is chloro. The group $R^5$ is preferably H or $C_{1-4}$ alkyl, most preferably H.

The oxidation may be suitably performed at moderate temperatures of from 0° to 50° C., usually at less than 25° C. The reaction may be continued for extended periods of from 1 to 72 hours until a reasonable yield of desired product is achieved. This will generally be dependent upon the nature of the reactants and catalysts employed.

The reaction is carried out at a pH in the range 7-11, preferably 8-10, even more preferably at a constantly maintained pH of 9-9.5 and most preferably at a constant pH of 9.

Suitable organic solvents include halogenated alkanes and arenes such as dichloromethane, chloroform, ethylene dichloride, chlorobenzene, dichlorobenzene; alkanes and cyloalkanes such as hexane and cyclohexane or esters such as ethyl acetate and isopropyl acetate.

The selection of a suitable phase transfer catalyst can be determined by routine procedures well known to the skilled chemist. Known phase transfer catalysts include tetralkyl ammonium halides and phosphonium salts. Preferred catalysts are tetralkyl ammonium halides, especially tetrabutyl ammonium chloride. The phase transfer catalyst is generally used at 1-10 mol %.

The oxidation catalyst comprising a ruthenium or palladium compound may be for example ruthenium chloride, $RuCl_2(PPh_3)_3$, ruthenium dioxide supported on an inert carrier such as silica or titania or palladium on carbon. A preferred oxidation catalyst is ruthenium chloride. The amount of ruthenium or palladium catalyst should be sufficient to catalyse the reaction in a reasonable timescale. This will depend upon many factors including the catalyst selected, the nature of the compounds of formula (II) and other reaction conditions. In general 0.01 mol % to 5 mol % of ruthenium or palladium catalyst is suitable.

The reaction may be performed as a batch process or as a continuous process.

Unreacted starting materials may be re-cycled, optionally with the addition of further oxidation catalyst and phase transfer catalyst. Further starting material may be added to the recycled liquors.

The invention will now be illustrated by reference to the following Example.

EXAMPLE 1

2-chloro-4-methylsulphonyltoluene (20.47 g, 0.1 moles), tetrabutyl ammonium chloride (1.46 g, 0.0053 moles), ruthenium chloride trihydrate (0.23 g, 0.0011 moles washed into the reactor with water) and 1,2-dichloroethane (55.4 g, 0.57 moles) were charged into a 500 ml round bottom flask.

Sodium hypochlorite (119.12 g, 1.6 moles) was pumped into the reaction flask over a 1 hour period (pH adjusted automatically to pH 9 using 20% sulphuric acid 2 minutes into addition) then maintained at pH 9 automatically using 10% sodium hydroxide for a further hour.

The reaction was agitated at 570 r.p.m. and the temperature controlled at <25° C. throughout.

The reaction mass was diluted with water to dissolve any precipitated sodium salt of the product, the phases separated and the aqueous phase filtered through a bed of clarcel flo filter aid to remove the ruthenium catalyst. The aqueous phase was acidified with 20% sulphuric acid and the precipitated product filtered off, washed with water and dried to yield 2-chloro-4-methylsulphonylbenzoic acid, (15.27 g, yield 51.5%), m.p. 189° C.

EXAMPLE 2

2-Chloro-4-methylsulphonyl toluene (14.2 g), tetrabutylammonium chloride (1.599 g), and ruthenium trichloride (0.602 g) were charged to a 200 ml jacketed reaction flask fitted with condenser, thermometer and pH probe. Ethyl acetate (30.7 g) was charged to the materials and the contents of the reactor agitated to dissolve the solids present. Sodium hypochlorite (12% active chlorine content) (9.5 g) was charged to the reactor and the pH of the mixture adjusted to pH 9±0.2 with sulphuric acid and sodium hydroxide liquors as required. More sodium hypochlorite (184 g) was then charged slowly to the reactor the pH being maintained at 9 to 9.5 by the addition of sodium hydroxide as required, the temperature was allowed to rise to 25° to 28° C. during this time, controlled if necessary with water on the reactor jacket. When all of the hypochlorite was charged the reaction mass was left stirring for 6 hours at room temperature, the reactor was tested with starch iodide to ensure some hypochlorite was present and if necessary a drop or two of hypochlorite was added. The agitation was stopped and the lower aqueous phase was separated off.

The lower aqueous phase was then agitated and heated to 50° C. then acidified to pH 2 with hydrochloric acid to precipitate the 2-chloro-4-methylsulphonylbenzoic acid product. The reaction mixture was cooled to room temperature and the product was filtered off and washed with water.

The organic phase was re-cycled and an additional ethyl acetate and ruthenium trichloride charge (10% of the amounts used in the first reaction) introduced into the reaction vessel.

The reaction was then repeated with a further 193.5 g of sodium hypochlorite.

After four re-cycles the yield of 2-chloro-4-methylsulphonylbenzoic acid was 89%.

EXAMPLE 3

The procedure of Example 2 was repeated using dichloroethane as solvent in place of ethyl acetate. The yield of 2-chloro-4-methylsulphonylbenzoic acid was 88.6%.

CHEMICAL FORMULAE (IN DESCRIPTION)

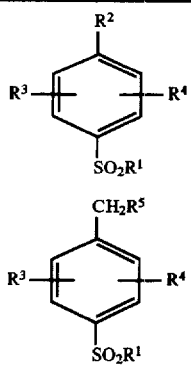

We claim:

1. A process for preparing a compound of formula (I),

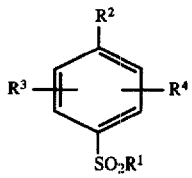

where $R^1$ is optionally substituted alkyl, $R^2$ is COOH, is selected from hydrogen, halo, haloalkyl, nitro, hydroxy, alkoxy, haloalkoxy or alkoxyalkoxy, and $R^4$ is selected from halo, haloalkyl, nitro, hydroxy alkoxy haloalkoxy or alkoxyalkoxy; which process comprises oxidising a compound of formula (II)

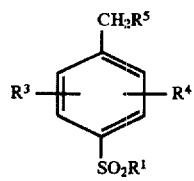

where $R^1$, $R^3$ and $R^4$ are as defined in relation to formula (I) and $R^5$ is H, halo or $C_{1-4}$ alkyl with sodium hypochlorite or sodium chlorite in the presence of a catalytic amount of a ruthenium or palladium compound and a phase transfer catalyst in an organic solvent at a pH of 7–11.

2. A process according to claim 1 wherein the reaction is performed at 0°–50° Ga.

3. A process according to claim 2 wherein the reaction is carried out at 0°–25° C.

4. A process according to claim 1 wherein the reaction is performed at a constantly maintained pH of 9–9.5.

5. A process according to claim 4 wherein the reaction is performed at 0°–50° C.

6. A process according to claim 5 wherein the reaction is carried out at 0°–25° C.

7. A process according to claim 1 wherein the ruthenium or palladium compound is ruthenium trichloride.

8. A process according to claim 2 wherein the ruthenium or palladium compound is ruthenium trichloride.

9. A process according to claim 3 wherein the ruthenium or palladium compound is ruthenium trichloride.

10. A process according to herein the ruthenium or palladium compound is ruthenium trichloride.

11. A process according to claim 1 wherein the phase transfer catalyst is tetrabutylammonium chloride.

12. A process according to claim 2 wherein the phase transfer catalyst is tetrabutylammonium chloride.

13. A process according to claim 3 wherein the phase transfer catalyst is tetrabutylammonium chloride.

14. A process according to claim 4 wherein the phase transfer catalyst is tetrabutylammonium chloride.

15. A process according to claim 7 wherein the phase transfer catalyst is tetrabutylammonium chloride.

16. A process according to claim 1 wherein $R^1$ is $CH_3$.

17. A process according to claim 1 wherein $R^5$ is H.

18. A process according to claim 16 wherein $R^5$ is H.

19. A process according to claim 1 wherein $R^3$ is H and $R^4$ is ortho to the group $R^2$.

20. A process according to claim 16 wherein $R^3$ is H and $R^4$ is ortho to the group $R^2$.

21. A process according to claim 18 wherein $R^3$ is H and $R^4$ is ortho to the group $R^2$.

22. A process according to claim 1, further comprising the steps of removing the compound of formula (I) from the reaction mixture and then recycling any unreacted starting materials remaining in the reaction mixture by repeating said process using said unreacted starting materials therein.

23. A process for preparing a compound of formula (I'),

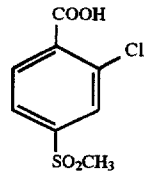

which process comprises oxidizing a compound of formula (II')

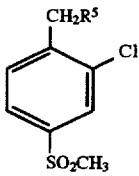

wherein $R^5$ is H, halo or $C_{1-4}$ alkyl, with sodium hypochlorite or sodium chlorite in the presence of a catalytic amount of a ruthenium or palladium compound and a phase transfer catalyst is an organic solvent at a pH of 7–11.

24. A process according to claim 23, wherein the reaction is performed at 0°–50° C.

25. A process according to claim 24, wherein the reaction is performed at 0°–25° C.

26. A process according to claim 23, wherein the reaction is performed at a constantly maintained pH of 9–9.5.

27. A process according to claim 23, wherein the ruthenium or palladium compound is ruthenium trichloride.

28. A process according to claim 23, wherein the phase transfer catalyst is tetrabutylammonium chloride.

29. A process according to claim 28, further comprising the steps of removing the compound of formula (I') from the reaction mixture and then recycling any unreacted starting materials remaining in the reaction mixture by repeating said process using said unreacted starting materials therein.

* * * * *

UNITED STATES PATENT AND TRADEMARK OFFICE
CERTIFICATE OF CORRECTION

PATENT NO. : 5,783,729

DATED : July 21, 1998

INVENTOR(S) : Stephen Martin Brown et al.

It is certified that error appears in the above-identified patent and that said Letters Patent is hereby corrected as shown below:

Column 3, line 51, claim 1, after "$R^2$ is COOH," insert -- $R^3$ --.

Column 4, line 5, claim 2, delete "Ga." and insert --C.--.

Signed and Sealed this

Twenty-sixth Day of January, 1999

Attest:

Attesting Officer

*Acting Commissioner of Patents and Trademarks*